US008669420B2

(12) United States Patent
Arrieta

(10) Patent No.: US 8,669,420 B2
(45) Date of Patent: Mar. 11, 2014

(54) HYBRID ARTICHOKE VARIETY NUN 4060 AR

(75) Inventor: Ignacio Susin Arrieta, Huesca (ES)

(73) Assignee: Nunhems B.V., AC Nunhem (NL)

( * ) Notice: Subject to any disclaimer, the term of this patent is extended or adjusted under 35 U.S.C. 154(b) by 0 days.

(21) Appl. No.: 13/408,535

(22) Filed: Feb. 29, 2012

(65) Prior Publication Data

US 2012/0227122 A1    Sep. 6, 2012

(51) Int. Cl.
*A01H 5/00*    (2006.01)
*A01H 5/10*    (2006.01)
*A01H 4/00*    (2006.01)
*A01H 1/02*    (2006.01)
*C12N 15/82*    (2006.01)

(52) U.S. Cl.
USPC ............ 800/298; 800/260; 800/268; 800/278

(58) Field of Classification Search
None
See application file for complete search history.

(56) References Cited

U.S. PATENT DOCUMENTS

2009/0044299 A1    2/2009    Colfer

FOREIGN PATENT DOCUMENTS

WO    2006108697    10/2006
WO    2007128559    11/2007

OTHER PUBLICATIONS

PVP 9000179 (Plant Variety Protection No. 9000179, Jan. 31, 1991).*

UPOV descriptors, Guidelines for the Conduct of Tests for Distinctness, Uniformity and Stability, TG/184/3 (Geneva 2001), as published by UPOV (International Union for the Protection of New Varieties and Plants, www.upov.int/en/publications/tg_rom/tg_index.html.
USDA descriptors are the plant variety descriptors for muskmelon/Cantaloupe (*Cucumis melo* L.) as published by the US Department of Agriculture, http://www.ams.usda.gov/AMSv1.0.
Pieter Vos et al., AFLP: A new technique for DNA fingerprinting 1995, Nucleic Acids Research (1995) vol. 23, No. 21, pp. 4407-4414.
A. B. Pisanu et al., Yield and Biometric Characteristics of 9 Clones Selected From the Population of "Spinoso Sardo" Artichokes, Acta Hort. (2004) vol. 660, pp. 83-89.
Eugenia Martin et al., Identification of markers linked to agronomic traits in globe artichoke, Australian Journal of Crop Science (2008) vol. 1(2), pp. 43-46.
Yehuda Basnitzki et al., A Seed-planted Cultivar of Globe Artichoke, HortScience (1987) vol. 22(4), pp. 678-679.
D Meyer et al., The bifidogenic effect of inulin and oligofructose and its consequences for gut health, European Journal of Clinical Nutrition (2009) vol. 63, pp. 1277-1289.
Smith et al., University of California, Division of Agriculture and Natural Resources publication 7221, "Artichoke production in California," and the world wide web at anrcatalog.ucdavis.edu for cultivation, harvesting, handling and postharvest methods commonly used / http://anrcatalog.ucdavis.edu/pdf/7221.pdf, published 2008.
Edward J. Ryder, The Globe Artichoke (*Cynara scolymus* L.), HortScience (1983) vol. 18(5), pp. 646-653.
Pecaut, P., et al., Intérêt des plants sains d'artichaut régénérés par la culture <<in vitro>>, P.H.M., Revue Horticole, 256, Apr. 1985.

* cited by examiner

*Primary Examiner* — Shubo (Joe) Zhou
*Assistant Examiner* — Keith Robinson

(57) ABSTRACT

The present invention provides a new and distinct hybrid variety of globe artichoke NUN 4060 AR. The new variety is to of the Camus type having large flat, pale green heads, and is relatively early maturing and produces heads suitable for both the fresh market and/or the processing industry.

19 Claims, No Drawings

HYBRID ARTICHOKE VARIETY NUN 4060 AR

FIELD OF THE INVENTION

The present invention relates to the field of plant breeding. In particular, a new and distinct hybrid variety of Globe artichoke is provided, designated NUN 4060 AR. The new variety is of the Camus De Bretagne type, having large flat, pale green heads, NUN 4060 AR, which is relatively early maturing and produces heads suitable for both the fresh market and/or the processing industry. The plants of NUN 4060 AR are most similar to the commercial variety Madrigal F1, which is a processing variety sold by Nunhems B. V. However, NUN 4006 AR differs from Madrigal F1 in a number of characteristics and can easily be distinguished from Madrigal when grown under the same environmental conditions. The plants grown from NUN 4060 AR seeds are tall plants, but on average slightly smaller than the very tall Madrigal plants. Also the number of days plants of NUN 4060 AR are in the harvest period is significantly less than those of Madrigal. The leaves of both varieties are similar (long leaves with incisions, slightly erect, without spines), but the leaves of NUN 4060 AR are on average shorter than those of Madrigal and the leaf color is gray-green, while that of Madrigal is dark green. Provided are seeds of NUN 4060 AR, plants and plant parts produced from these seeds (such as heads, hearts, bottoms, etc.), vegetative reproductions of the variety NUN 4006 AR, and progeny of the variety.

SUMMARY OF THE INVENTION

The invention provides for a new hybrid variety of Globe artichoke called NUN 4060 AR. The invention also provides for a plurality of seeds of the new variety, plants produced from growing the seeds and plant parts obtainable from the grown plant, such as (harvested) flower heads, or parts of the flower heads (e.g. hearts, bottoms, etc).

Thus, in one aspect, the invention provides seeds of artichoke variety designated NUN 4060 AR, wherein a representative sample of seeds of said variety was deposited under the Budapest Treaty, with Accession number NCIMB 42171.

In another aspect, the invention provides for an artichoke plant of artichoke variety NUN 4060 AR, a representative sample of seed from said variety has been deposited under the Budapest Treaty, with Accession number NCIMB 42171.

In other aspects, the invention provides for plant parts, such as pollen, flower heads, hearts, bottoms, bracts, shoots, cuttings, receptacles of variety NUN 4060 AR or parts thereof.

In other aspects, the invention provides for progeny of variety NUN 4060 AR such as progeny obtained by selfing NUN 4060 AR one or more times and/or cross-pollinating NUN 4060 AR with another Globe artichoke plant or variety one or more times. In particular, the invention provides for progeny that retain all the morphological and physiological characteristics of NUN 4060 AR when grown under the same environmental conditions. In another aspect, the invention provides for vegetative reproductions of the variety are provided and essentially derived varieties (EDVs) of NUN 4060 AR.

DEFINITIONS

"Artichoke" or "Globe artichoke" refers herein to plants of the species *Cynara scolymus* L. (synonym *Cynara cardunculus* var. *scolymus* L.).

"Flower head" or "head" refers to immature flower heads (also called "flower buds" or "capitulates"), harvested or on the plant. The "central flower head" refers to the terminal flower head produced on the central, main stem. Other flower heads are produced on lateral branches.

"Heart" is the edible part of the flower head comprising or consisting of the fleshy receptacle (or a part thereof) with the fleshy base of the inner bracts (or parts thereof). "Artichoke bottom" is the edible fleshy lower part of the heart.

"UPOV descriptors" are the plant variety descriptors described for Globe Artichoke in the "Guidelines for the Conduct of Tests for Distinctness, Uniformity and Stability, TG/184/3 (Geneva 2001), as published by UPOV (International Union for the Protection of New Varieties and Plants, available on the world wide web at upov.int) and which can be downloaded from the world wide web at upov.int/en/publications/tg_rom/tg_index.html and is herein incorporated by reference in its entirety.

As used herein, the term "plant" includes the whole plant or any parts or derivatives thereof, preferably having the same genetic makeup as the plant from which it is obtained, such as plant organs (e.g. harvested or non-harvested heads, hearts, receptacles), plant cells, plant protoplasts, plant cell tissue cultures from which whole plants can be regenerated, plant calli, plant cell clumps, plant transplants, seedlings, plant cells that are intact in plants, plant clones or micropropagations, or parts of plants (e.g. harvested tissues or organs), such as plant cuttings, vegetative propagations, embryos, pollen, ovules, fruits, flowers, leaves, seeds, clonally propagated plants, roots, stems, root tips, grafts, parts of any of these and the like. Also any developmental stage is included, such as seedlings, cuttings prior or after rooting, mature plants or leaves.

"Harvested plant material" refers herein to plant parts (e.g. heads detached from the whole plant or hearts removed from the heads) which have been collected for further storage and/or further use.

"Harvested seeds" refers to seeds harvested from a line or variety, e.g. produced after self-fertilization or cross-fertilization and collected.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A variety is referred to as an "Essentially Derived Variety" (EDV) is a variety (i.e., shall be deemed to be essentially derived from another variety, "the initial variety") when (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, the selection of a variant individual from plants of the initial variety, backcrossing, or transformation by genetic engineering.

"Plant line" is for example a breeding line which can be used to develop one or more varieties.

"Hybrid variety" or "F1 hybrid" refers to the seeds harvested from crossing two inbred parental lines. For example, the female parent is pollinated with pollen of the male parent to produce hybrid (F1) seeds on the female parent.

"Average" refers herein to the arithmetic mean.

Locus (plural loci) refers to the specific location of a gene or DNA sequence on a chromosome. A locus may confer a specific trait.

DETAILED DESCRIPTION

Globe artichoke is a vegetable crop originating from the Mediterranean region. The immature flower heads (also called "globes") contain edible parts, the fleshy bracts and hearts, which can be harvested for the fresh market or for industrial purposes (e.g. the canning industry). Certain extracts are also used in the pharmaceutical field.

Artichoke is predominantly cross-pollinating (due to the stigmatic surfaces maturing several days after pollen shedding) and selfing can result in some inbreeding depression. Artichoke cultivars have traditionally been bred as clones, using vegetative propagation (planting of basal stumps or suckers), because seed populations were not uniform enough for cultivation. In recent years seed propagated hybrid cultivars have been developed which do have good uniformity, such as Madrigal F1, Concerto F1 and others. These hybrids are produced from true breeding inbred parental lines.

The shift to seed-planted varieties (rather than vegetative cultivation) has enabled artichoke to be grown as an annual crop, although seed-planted varieties can also be grown as perennials. Seed-planted varieties are cost and labor saving, because seeds are sown mechanically. Also yields and quality are much higher, probably to some extent due to the fact that direct-seeded plants produce long taproots, which penetrate deeper into the soil than the vegetative plantations. Hybrid vigor also plays a role in improved yields, as does the better pest and disease control of annually seeded crops. Although a number of (seed-planted) hybrid varieties exist, there is still a need for new, high yielding, uniform hybrids with good head quality.

A number of characteristics are important to artichoke breeders including (a) the time of harvest (varieties adapted to early or late harvest); (b) the size and quality of the heads (determining whether the heads are suitable for fresh and/or industry purposes); (c) the shape of the heads; (d) the size of the plant; and (e) the spinelessness of the bracts.

The present invention provides a new artichoke of the Camus type having large flat, pale green heads, NUN 4060 AR, which is relatively early maturing and produces heads suitable for both the fresh market and/or the processing industry. The plants of NUN 4060 AR are most similar to the commercial variety Madrigal F1, which is a processing variety sold by Nunhems B. V. However, NUN 4060 AR differs from Madrigal F1 in a number of characteristics and can easily be distinguished from Madrigal when grown under the same environmental conditions, see Table 1. Firstly, the plants grown from NUN 4060 AR seeds are tall plants (measured from the soil to the top of the central flower head), but on average slightly smaller than the very tall Madrigal plants. Also the number of days plants of NUN 4060 AR are in the harvest period is significantly lower, at least about 30, 35, 40, 45, preferably at least 50, 54, 58, 60 or 62 days less than that of Madrigal. The leaves of both varieties are similar (long leaves with incisions, slightly erect, without spines), but the leaves of NUN 4060 AR are on average shorter than those of Madrigal and the leaf color is gray-green, while those of Madrigal dark green.

In addition, the primary head shape of NUN 4060 AR is oblate, while that of Madrigal is ovoid. The weight of the primary head of NUN 4060 AR is significantly higher than that of Madrigal while the average weight of the secondary flower head is slightly lower. The primary head length of NUN 4060 AR is somewhat shorter than that of Madrigal.

As discussed herein, one of the main differences between NUN 4060 AR and Madrigal F1 is the number of days in the harvest period, which is relatively short in NUN 4060 F1 compared to Madrigal when grown under the same environmental conditions.

The outer bracts of the flower heads are mainly light green with no secondary color, while in Madrigal the external bract main color is mid green with a brown tint as secondary color on the tip. The internal bract color of NUN 4060 AR is whitish-green, while that of Madrigal F1 is yellow-green.

The morphological and/or physiological differences between NUN 4060 AR and other known varieties can easily be established by growing NUN 4060 AR next to the other varieties (in the same field, under the same environmental conditions), preferably in several locations which are suitable for artichoke cultivation, and measuring morphological and/or physiological characteristics of a number of plants (e.g., to calculate an average value and to determine the variation range/uniformity within the variety).

For example, trials can be carried out in California, USA, whereby e.g., plant height, width, growth habit, side shoot number, foliage density, head size, head shape, head number, head texture, head fragrance, head weight, bract size, bract shape, bract texture, bract number, bract color, bract basal thickness, heart shape and size, heart color, papus length and color, head firmness, bract firmness, head gloss, leaf length and width, leaf incisions (serrations), leaf basal angle, leaf length to width ratio, leaf color, leaf texture, leaf venation, leaf basal thickness, distance between incisions, petiole length and width, pest and/or disease resistance/susceptibility can be measured and directly compared. Also post-harvest characteristics of heads can be compared, such as cold storage holding quality (browning), post-harvest oxidation of heads, and juiciness can be measured using known methods (see e.g., US 2009/0044299, paragraph 0016). The morphological and/or physiological characteristics may vary with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (http://www.rhs.org.uk/Plants/RHS-Publications/RHS-colour-charts).

Seeds of artichoke variety NUN 4060 AR are provided herein, wherein a representative sample of said seeds (2500 seeds) has been deposited, under the Budapest Treaty, with Accession Number NCIMB 42171.

Seeds of NUN 4060 AR are obtainable by crossing the male parent with the female parent and harvesting the seeds produced on the female parent. The resultant NUN 4060 AR seeds can be grown to produce NUN 4060 AR plants. In one embodiment a plurality of NUN 4060 AR seeds are packaged into small and/or large containers (e.g., bags, cartons, cans, etc.). The seeds may be treated with various compounds, such as seed coatings.

Also provided are plants of artichoke variety NUN 4060 AR, or a part thereof, produced from seeds, wherein a representative sample of said seeds has been deposited under the Budapest Treaty, with Accession Number NCIMB 42171. Plants of NUN 4060 AR can be produced by seeding directly in the ground (e.g., field) or by germinating the seeds in controlled environment conditions (e.g., greenhouses) and then transplanting the seedlings into the field. (See Smith et al., University of California, Division of Agriculture and Natural Resources publication 7221, "Artichoke production in California," and the world wide web at anrcatalog.ucdavis.edu for cultivation, harvesting, handling and postharvest methods commonly used).

Parts of NUN 4060 AR encompass any cells, tissues, organs obtainable from the seedlings or plants, such as but not limited to: heads or parts thereof, hearts, bottoms, bracts, cuttings, pollen and the like. Such parts can be stored and/or processed further. Encompassed are therefore also food or feed products comprising one or more of such parts, such as canned hearts or bottoms obtainable from NUN 4060 AR or from progeny thereof, or from a derived variety, such as an EDV.

In a preferred embodiment, the invention provides for heads of artichoke variety NUN 4060 AR, or a part of the head. The heads are preferably harvest-stage heads. They may be harvested (e.g., manually, by removing the heads from the remaining plant) and stored and/or processed further. In another embodiment, the invention provides for a container comprising or consisting of a plurality of harvested heads of NUN 4060 AR, or progeny thereof, or a derived variety, such as an EDV.

In yet a further embodiment, the invention provides for a method of producing a new artichoke plant. The method comprises crossing NUN 4060 AR, either as male or as female parent, with a second artichoke plant (or a wild relative of artichoke) one or more times, and/or selfing NUN 4060 AR one or more times, and selecting progeny from said crossing and/or selfing. Progeny are either the generation (seeds) produced from the first cross (F1) or selfing (S1), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g. the F2) with another artichoke plant (and/or with a wild relative of artichoke). Using common breeding methods such as backcrossing or recurrent selection, one or more specific characteristics may be introduced into NUN 4060 AR, to provide an EDV of NUN 4060 AR.

A "wild" relative of artichoke is herein selected from *Cynara cardunculus* var. *sylvestris* (wild cardoon), *Cynara cardunculus* subsp *cardunculus* (cultivated cardoon), *C. baetica, C. algarbiensis, C. syriaca, C. cornigera, C. cyrenaica, C. humilis* and *C. trournefortii*.

The invention provides for methods of producing varieties which retain all the morphological and physiological characteristics of NUN 4060 AR, or EDVs (Essentially Derived Varieties), which may differ from NUN 4060 AR in one, two, three or more morphological and/or physiological characteristics, but which are still genetically closely related to NUN 4060 AR. The relatedness can, for example be determined by fingerprinting techniques (e.g., making use of isozyme markers and/or molecular markers such as SNP markers, AFLP markers, microsatellites, minisatellites, RAPD markers, RFLP markers and others). An plant is "closely related" to NUN 4060 AR if its DNA fingerprint is at least 80%, 90%, 95% or 98% identical to the fingerprint of NUN 4060 AR. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Pisanu et al. ISHS 2004, Acta Hort. 660).

The invention further provides a method of introducing a single locus conversion into NUN 4060 AR comprising (a) crossing a plant of variety NUN 4060 AR, a representative sample of seed of said variety having been deposited under Accession Number NCIMB 42171, with a second plant comprising a desired single locus to produce F1 progeny plants; (b) selecting F1 progeny plants that have the single locus to produce selected F1 progeny plants; (c) crossing the selected progeny plants with at least a first plant of NUN 4060 AR to produce backcross progeny plants; (d) selecting backcross progeny plants that have the single locus and physiological and morphological characteristics of NUN 4060 AR to produce selected backcross progeny plants; and (e) repeating steps (c) and (d) one or more times in succession to produce selected second or higher backcross progeny plants that comprise the single locus and otherwise comprise all of the physiological and morphological characteristics of NUN 4060 AR when grown in the same environmental conditions.

By crossing and/or selfing also (one or more) single traits may be introduced into NUN 4060 AR (e.g., using backcrossing breeding schemes), while retaining the remaining morphological and physiological characteristics of NUN 4060 AR. For example, disease resistance genes may be introduced, genes responsible for one or more quality traits (such as head quality), yield, etc. Both single genes (dominant or recessive) and one or more QTLs (quantitative trait loci) may be transferred into NUN 4060 AR by breeding with NUN 4060 AR.

Any pest or disease resistance genes may be introduced into NUN 4060 AR, progeny thereof or into an EDV of NUN 4060 AR. Resistance to one or more of the following diseases is preferably introduced into plants of the invention: Powdery mildew, *Verticillium* wilt (*V. dahliae*), *Botrytis* rot, Curly Dwarf Virus and Bacterial Crown rot. Resistance to one or more of the following pests is preferably present or introduced into plants of the invention: artichoke plume moth (*Platyptilia caduidactyla*), artichoke moth (*Gortyna xantheses*), aphid resistance, proba bug resistance, two-spotted spider-mite resistance, *Chrysanthemum* leaf-miner, and Cribate weevil resistance. Other resistance genes, against pathogenic viruses (e.g. Artichoke Latent Virus, ArLV; artichoke mottled crinkle virus, AMCV; Tomato Spotted Wilt Virus, TSWV; Inpatiens necrotic spot virus, INSV; Cucumber mosaic virus, CMV), fungi, bacteria or artichoke pests may also be introduced.

Thus, invention also provides a method for developing an artichoke plant in an artichoke breeding program, using an artichoke plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 4060 AR or progeny thereof with a different artichoke plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Martin et al. 2008, Australian Journal of Crop Science 1(2): 43-46). For breeding methods in general see Principles of Plant Genetics and Breeding, 2007, George Acquaah, Blackwell Publishing, ISBN-13:978-1-4051-3646-4.

A method of introducing a single locus conversion into NUN 4060 AR is provided comprising (a) crossing a plant of variety NUN 4060 AR, a representative sample of seed of said variety having been deposited under Accession Number NCIMB 42171, with a second plant comprising a desired single locus to produce F1 progeny plants;

(b) selecting F1 progeny plants that have the single locus to produce selected F1 progeny plants;

(c) crossing the selected progeny plants with at least a first plant of NUN 4060 AR to produce backcross progeny plants;

(d) selecting backcross progeny plants that have the single locus and physiological and morphological characteristics of NUN 4060 AR to produce selected backcross progeny plants; and (e) repeating steps (c) and (d) one or more times in succession to produce selected second or higher backcross progeny plants that comprise the single locus and otherwise comprise all of the physiological and morphological characteristics of NUN 4060 AR when grown in the same environmental conditions.

The above method is provided, wherein the single locus confers a trait, wherein the trait is pest resistance or disease resistance.

In one embodiment the trait is disease resistance and the resistance is conferred to powdery mildew, *Verticillium* wilt, *Botrytis* rot, Curly Dwarf Virus, or Bacterial Crown rot.

In one embodiment the trait is pest resistance and the resistance is conferred to artichoke plume moth, artichoke moth, aphid resistance, proba bug resistance, two-spotted spider-mite resistance, Chrysanthemum leaf-miner, or Cribate weevil.

In one embodiment, NUN 4060 AR may also be mutated (by e.g. irradiation, chemical mutagenesis, heat treatment, etc.) and mutated seeds or plants may be selected in order to change one or more characteristics of NUN 4060 AR. Also natural mutants may be identified and used in breeding. Methods such as TILLING and/or EcoTILLING may be applied to artichoke populations in order to identify mutants. Similarly, NUN 4060 AR may be transformed and regenerated, whereby one or more chimeric genes are introduced into the variety. Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 4060 AR, or progeny thereof, by transforming NUN 4060 AR or progeny thereof with a transgene that confers the desired trait, wherein the transformed plant retains all the morphological and physiological characteristics of NUN 4060 AR or the progeny thereof and contains the desired trait.

The invention also provides for progeny of artichoke variety NUN 4060 AR obtained by further breeding with NUN 4060 AR. In one aspect progeny are F1 progeny obtained by crossing NUN 4060 AR with another plant or S1 progeny obtained by selfing NUN 4060 AR. Also encompassed are F2 progeny obtained by selfing the F1 plants. "Further breeding" encompasses traditional breeding (e.g., selfing, crossing, backcrossing), marker assisted breeding, and/or mutation breeding. In one embodiment, the progeny have all the physiological and morphological characteristics of variety NUN 4060 AR when grown under the same environmental conditions. In another embodiment the progeny are EDVs and/or have one, two, or three distinct traits (qualitative or quantitative) introduced into NUN 4060 AR, while retaining all the other physiological and morphological characteristics of variety NUN 4060 AR when grown under the same environmental conditions.

The variety NUN 4060 AR, or its progeny (e.g. an EDV), can also be reproduced using vegetative reproduction methods. Therefore, the invention provides for a method of producing plants, or a part thereof, of variety NUN 4060 AR comprising vegetative propagation of variety NUN 4060 AR. Vegetative propagation comprises regenerating a whole plant from a part of variety NUN 4060 AR, such as a cutting, a cell culture or a tissue culture (e.g., in vitro meristem culture, see Pecaut et al. 1985, Revue Horticuole 256: 21-26), a "stump" (basal stem piece with attached root sections or a rooted section of the crown), suckers derived from NUN 4060 AR, shoot or offshoots derived from NUN 4060 AR or ovoli derived from NUN 4060 AR (see Ryder et al., 1983, Hort Science 18: 646-653).

The invention also provides for a vegetatively propagated plant of variety NUN 4060 AR, or a part thereof, having all the morphological and physiological characteristics of NUN 4060 AR when grown under the same environmental conditions.

In one aspects haploid plants and/or double haploid plants of NUN 4060 AR are encompassed herein. Haploid and double haploid (DH) plants can for example be produced by anther or microspore culture and regeneration into a whole plant. For DH production chromosome doubling may be induced using known methods, such as colchicine treatment or the like.

Also provided are plant parts derived from variety NUN 4060 AR, or from a vegetatively propagated plant of NUN 4060 AR, being selected from the group consisting of: harvested flower heads or parts thereof, pollen, cells, leaves or parts thereof, petioles, shoots or parts thereof, stems or parts thereof, roots or parts thereof, cuttings, stumps, suckers, offshoots, ovoli, receptacles or parts thereof, bracts or parts thereof, flowers, florets, or flower buds.

Globe artichoke leaves represent a natural source of phenolic acids with dicaffeoylquinic acids, such as cynarin (1,3-dicaffeoylquinic acid), along with its biosynthetic precursor chlorogenic acid (5-caffeoylquinic acid) as the most abundant molecules. In various pharmacological test systems, artichoke leaf extracts have exhibited hepatoprotective, anticarcinogenic, antioxidative, antibacterial, anti-HIV, bile-expelling, and urinative activities as well as the ability to inhibit cholesterol biosynthesis and LDL oxidation. These broad therapeutic indications probably cannot be ascribed to a single, but to several active compounds that together generate additive or synergistic pharmacologic effects; these include mono- and dicaffeoylquinic acids, and flavonoids such as luteolin and its 7-O-glucoside. Artichoke tissues such as leaves, external bracts and stems can be used as a source of inulin and/or phenolics, useful for the production of food additives and nutraceuticals.

In one embodiment, the invention provides for extracts of a plant described herein and compositions comprising or consisting of such extracts. In a preferred embodiment, the extract consists of or comprises tissue of a plant described herein or is obtained from such tissue. For example cynarin may be an extract obtained from leaf tissue and used to make a health-beneficial composition (e.g., a pharmaceutical composition or a food supplement). Likewise inulin (e.g., very long chain inulin, VLCI) may be extracted from globe artichoke tissue, such as roots and used in food or feed, food supplement, pharmaceutical or nutraceutical compositions. VLCI from Globe artichoke has health beneficial properties, e.g., on gut-health, see e.g. WO 2006/108697, WO2007/

128559 and Meyer and Stasse-Wolthuis, 2009 (European Journal of Clinical Nutrition 63, 1277-1289.

The invention also provides for a food or feed product comprising or consisting of a plant part described herein and/or an extract from a plant part described herein. The food or feed product may be fresh or processed, e.g., canned, steamed, boiled, fried, blanched and/or frozen, etc.

For example, containers such as cans, boxes, crates, bags, cartons, Modified Atmosphere Packagings, films (e.g. biodegradable films), etc. comprising plant parts of plants (fresh and/or processed) described herein are also provided herein.

Marketable heads are generally sorted by size and quality after harvest. Cartons may be packaged with "18s" (18 heads, each larger than 4.5 inches in diameter), "24s" (25 heads of 4-4.5 inches), "36s" (36 heads of 3.5-4 inches), "48$^{ths}$" (48 heads of 3-3.5 inches) or "60s" (60 heads of 2.75-3 inches). The harvested heads of NUN 4060 AR are most suitable for packaging with 24s (or 18s or 36s), see Examples regarding base head diameter of heads.

All documents (e.g., patent publications) are herein incorporated by reference in their entirety.

EXAMPLES

Development of NUN 4060 AR

The hybrid NUN 4060 AR was developed from a male and female proprietary inbred line of Nunhems. The female and male parents were crossed to produce hybrid (F1) seeds of NUN 4060 AR. The seeds of NUN 4060 AR can be grown to produce hybrid plants and parts thereof (e.g. flower heads). The hybrid NUN 4060 AR can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 4060 AR is uniform and stable.

A total of 2500 seeds of the hybrid variety NUN 4060 AR were deposited according to the Budapest Treaty by Nunhems B. V. on Oct. 10, 2013, at the NCIMB Ltd., Ferguson Building, Craibstone Estate, Bucksburn, Aberdeen AB21 9YA, United Kingdom (NCIMB). The deposit has been assigned Accession Number NCIMB 42171. Upon allowance of any claims in the application, the Applicants will make available to the public, pursuant to 37 C.F.R. §1.808, sample(s) of the deposit with the NCIMB.

A deposit of NUN 4060 AR and of the male and female parent line is also maintained at Nunhems B. V. Access to the deposit will be available during the pendency of this application to persons determined by the Director of the U.S. Patent Office to be entitled thereto upon request. Subject to 37 C.F.R.§1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

"USDA descriptors" are plant variety descriptors described for artichoke in the "Objective Description of Variety Artichoke (*Cyanara scoliymus* L.)—Exhibit C" of the U.S. Department of Agriculture, Agricultural Marketing Service, Science and Technology, Plant Variety Protection Office, Beltsville, Md. 20705, which can be downloaded from http://www.ams.usda.gov/AMSv1.0/ams .fetchTemplateData.do?template=TemplateJ&page =PVPO-Forms, and is herein incorporated by reference in its entirety. Useful publications as reference aids for completing this exhibit C form are Ryder, E. J., N. E. De Vos, and M. A. Bari. 1983 The globe artichoke (*Cynara scolymus* L.) HortSience 18(5):646-653; Basnitzki, Y. and D. Zohary. 1987 A seed-planted cultivar of globe artichoke. HortSience 22(4):678-679; Dellacecca, V., V. Magnifico, V. Marzi, E. Porceddu, and G. Mugnozza. 1974. Contributo alla conoscenza delle varieta' di cardiofo coltivate nel mondo (Description of artichoke vareities cultivated in the world). Nuovi Studi sul Carciofo. Paper from Second International Congress on Artichoke Studies pp. 199-315; these are incorporated by reference in their entirety.

The most similar variety to NUN 4060 AR is Madrigal. In Table 1 a comparison between NUN 4060 AR and Madrigal F1 is shown based on a trial in the USA. Trial location: River Rd Chualar, (coordinates: 36° 57' N., −121° 54' W.), USA 2010-2011. Mild weather conditions 13 to 24° C. Planting date: 22 May 2010. Drip irrigation. Two replication of 50 plants each, from which 15 plants or plant parts were randomly selected to measure characteristics. In Table 1 the USDA descriptors of variety artichoke *Cyanara scoliymus* are shown for both of NUN 4060 AR (this application) and Madrigal F1 (a seed propagated green hybrid variety sold by Nunhems B. V. for industrial use).

TABLE 1

Objective description of variety Artichoke NUN 4060 AR compared with Madrigal F1

| USDA Descriptor | NUN 4060 AR | Madrigal |
| --- | --- | --- |
| No. of days from seeding to first head harvest | 300 | 290 |
| No. of days in harvest period | 81 | 140 |
| Plant height (harvest stage) (cm) | 150.1 | 164.4 |
| Plant habit (harvest stage) | 1 | 1 |
| (1 = upright; 2 = Intermediate; 3 = Broad) | | |
| No. of axillary shoots (harvest stage) | 5.2 | 4.8 |
| Leaf (harvest stage) - color | 4 | 3 |
| Leaf Color: 1 = Light Green 2 = Medium Green 3 = Dark Green 4 = Gray-Green | | |
| Leaf (harvest stage) - spines | 1 | 1 |
| (1 = none; 2 = few; 3 = many) | | |
| Leaf (harvest stage) - blade length (cm) | 117.5 | 142.6 |
| Leaf (harvest stage) - blade width (cm) | 51.4 | 52.7 |
| Leaf (harvest stage) - shape | 3 | 3 |
| (1 = entire; 2 = slight lobed; 3 = deeply lobed) | | |

TABLE 1-continued

Objective description of variety Artichoke NUN 4060 AR compared with Madrigal F1

| USDA Descriptor | NUN 4060 AR | Madrigal |
|---|---|---|
| Leaf (harvest stage) - shape variability (1 = slight; 2 = moderate; 3 = high) | 2 | 2 |
| Primary flower head (harvest stage) - shape (1 = cylindrical; 2 = conical; 3 = ovoid; 4 = ellipsoid; 5 = oblate) | 5 | 3 |
| Primary flower head (harvest stage) - base diameter (cm) | 10.87 | 10.12 |
| Primary flower head (harvest stage) - head length or depth (cm) | 8.65 | 10.06 |
| Primary flower head (harvest stage) - bract tightness (1 = Loose; 2 = moderately compact; 3 = compact) | 2 | 3 |
| Primary flower head (harvest stage) - bract luster (1 = dull; 2 = shiny) | 1 | 1 |
| Primary flower head (harvest stage) - external bract main color (1 = light green; 2 = mid green; 3 = dark green; 4 = purple; 5 = other) | 1 | 2 |
| Primary flower head (harvest stage) - external bract secondary color (1 = none; 2 = purple tint; 3 = brown tint; 4 = green tint; 5 = purple-brown tint; 6 = other) | 1 | 3 |
| Primary flower head (harvest stage) - location of secondary color (1 = tip; 2 = center; 3 = base; 4 = throughout) | 0 | 1 |
| Primary flower head (harvest stage) - internal bract color (1 = whitish-green; 2 = yellow-green; 3 = straw) | 1 | 2 |
| Primary flower head (harvest stage) - bract spines (1 = none; 2 = few; 3 = many) | 1 | 1 |
| Primary flower head (harvest stage) - bract shape (1 = round; 2 = oval; 3 = elongated) | 3 | 3 |
| Primary flower head (harvest stage) - bract tip shape (1 = entire; 2 = slightly notched; 3 = deeply notched) | 3 | 2 |
| Primary flower head (harvest stage) - bract length (mm) | 54.80 | 57.5 |
| Primary flower head (harvest stage) -bract width (mm) | 30.03 | 32.55 |
| Primary flower head (harvest stage) - peduncle length (cm) | 16.22 | 12.89 |
| Primary flower head (harvest stage) - peduncle diameter (mm) | 30.53 | 28.29 |
| Primary flower head (harvest stage) - weight per primary head (g) | 449.70 | 430.64 |
| Primary flower head (harvest stage) - no. of primary heads per plant | 1 | 1 |
| Secondary flower head - weight per secondary head (g) | 228.70 | 239.46 |
| Secondary flower head - no. secondary heads per plant | 3.8 | 4.8 |
| Floret color (1 = white; 2 = pink; 3 = red; 4 = purple; 5 = blue; 6 = other) | 4 | 4 |
| Achene color (1 = monocolor; 2 = bicolor) | 2 | 2 |
| Achene color pattern (1 = solid; 2 = speckling; 3 = striping; 4 = other) | n.r. | n.r. |
| Achene primary color (1 = tan; 2 = brown; 3 = green; 4 = black; 5 = grey) | n.r. | n.r. |
| Achene secondary color (1 = tan; 2 = brown; 3 = green; 4 = black; 5 = grey) | n.r. | n.r. |
| Anthocyanin Leaf Petiole 1 = Absent; 2 = Noticable; 3 = Very Noticable | 2 | 2 |
| Anthocyanin Leaf Blade 1 = Absent; 2 = Noticable; 3 = Very Noticable | 1 | 1 |
| Anthocyanin Peduncle 1 = Absent; 2 = Noticable; 3 = Very Noticable | 1 | 1 |
| Anthocyanin Petal 1 = Absent; 2 = Noticable; 3 = Very Noticable | 3 | 3 |
| Anthocyanin Head Bract 1 = Absent; 2 = Noticable; 3 = Very Noticable | 2 | 2 |
| Anthocyanin Bract Spine 1 = Absent; 2 = Noticable; 3 = Very Noticable | 1 | 1 |
| Anthocyanin Leaf Spine 1 = Absent; 2 = Noticable; 3 = Very Noticable | 1 | 1 |
| Anthocyanin Pappus 1 = Absent; 2 = Noticable; 3 = Very Noticable | 2 | 2 |
| Anthocyanin Achene 1 = Absent; 2 = Noticable; 3 = Very Noticable | 1 | 1 |
| Anthocyanin Other (specify) 1 = Absent; 2 = Noticable; 3 = Very Noticable | n.r. | n.r. |
| Disease Reaction - *Botrytis* Rot (*Botrytis cinerea*) (0 = not tested; 1 = susceptible; 2 = resistant) | n.r. | n.r. |

TABLE 1-continued

Objective description of variety Artichoke NUN 4060 AR compared with Madrigal F1

| USDA Descriptor | NUN 4060 AR | Madrigal |
|---|---|---|
| Disease Reaction - Curly Dwarf Virus (0 = not tested; 1 = susceptible; 2 = resistant) | n.r. | n.r. |
| Disease Reaction - Black tip Syndrome (0 = not tested; 1 = susceptible; 2 = resistant) | n.r. | n.r. |
| Disease Reaction - Other _____ (0 = not tested; 1 = susceptible; 2 = resistant) | n.r. | n.r. |
| Insect Reaction-Plume Moth (*Platyptillia carduidactyla*) (0 = not tested; 1 = susceptible; 2 = resistant) | n.r. | n.r. |
| Insect Reaction - Aphid (0 = not tested; 1 = susceptible; 2 = resistant) | n.r. | n.r. |
| Insect Reaction - 2-Spotted Spider Mite (0 = not tested; 1 = susceptible; 2 = resistant) | n.r. | n.r. |
| Insect Reaction - Chrysanthemum Leafminer (0 = not tested; 1 = susceptible; 2 = resistant) | n.r. | n.r. |
| Insect Reaction - Cribate Weevil (0 = not tested; 1 = susceptible; 2 = resistant) | n.r. | n.r. |
| Insect Reaction - Other _____ (0 = not tested; 1 = susceptible; 2 = resistant) | n.r. | n.r. |

These are typical values. Values may vary due to environment. Other values that are substantially equivalent are also within the scope of the invention.
n.r. = not recorded.

The invention claimed is:

1. A seed of artichoke variety NUN 4060 AR, wherein a representative sample of said seed has been deposited under Accession Number NCIMB 42171.

2. A plant of artichoke variety NUN 4060 AR, or a part thereof, wherein a representative sample of seed of said variety has been deposited under Accession Number NCIMB 42171.

3. A head of artichoke variety NUN 4060 AR, or a part thereof, produced from the plant of claim 2.

4. A method of producing an artichoke plant, comprising crossing the plant of claim 2 with a second artichoke plant one or more times, and selecting progeny from said crossing.

5. A method of producing an artichoke plant, comprising selfing the plant of claim 2 one or more times, and selecting progeny from said selfing.

6. Progeny of artichoke variety NUN 4060 AR obtained by further breeding with said variety, wherein said progeny have all the physiological and morphological characteristics of variety NUN 4060 AR when grown under the same environmental conditions.

7. An Essentially Derived Variety of NUN 4060 AR having one, two or three physiological and/or morphological characteristics which are different from those of NUN 4060 AR and which otherwise has all the physiological and morphological characteristics of NUN 4060 AR, wherein a representative sample of seed of variety NUN 4060 AR has been deposited under Accession Number NCIMB 42171.

8. A method of producing plants, or a part thereof, of variety NUN 4060 AR comprising vegetative propagation of variety NUN 4060 AR.

9. The method of claim 8, wherein said vegetative propagation comprises regenerating a whole plant from a part of variety NUN 4060 AR.

10. The method of claim 9, wherein said part is a cutting, a cell culture, a tissue culture, a stump, a sucker, a shoot, an offshoot or an ovoli.

11. A vegetative propagated plant of variety NUN 4060 AR, or a part thereof, having all the morphological and physiological characteristics of NUN 4060 AR when grown under the same environmental conditions.

12. Plant parts of variety NUN 4060 AR, or of a plant of claim 11, wherein said plant part are harvested flower heads or parts thereof, pollen, cells, leaves or parts thereof, petioles, shoots or parts thereof, stems or parts thereof, roots or parts thereof, cuttings, stumps, offshoots, ovoli, receptacles or parts thereof, bracts or parts thereof, flowers, florets, or flower buds, wherein a representative sample of seed of variety NUN 4060 AR has been deposited under Accession Number NCIMB 42171.

13. A food or feed product comprising a plant part of claim 12.

14. The food or feed product of claim 13, wherein said plant part is fresh or processed.

15. An artichoke plant produced by growing the seed of claim 1.

16. A method of producing an artichoke plant having a desired trait, wherein the method comprises transforming the artichoke plant of claim 2 with a transgene that confers the desired trait, wherein the transformed plant retains all the phenotypic and morphological characteristics of variety NUN 4060 AR and contains the desired trait, a representative sample of seed of said variety NUN 4060 AR having been deposited under Accession Number NCIMB 42171.

17. An artichoke plant produced by the methods of claims 16, wherein the plant comprises the desired trait and all of the physiological and morphological characteristics of NUN 4060 AR.

18. A cell or tissue culture produced from a plant of claim 2.

19. An artichoke plant regenerated from a cell or tissue culture of claim 18, said plant expressing all the morphological and physiological characteristics of NUN 4060 AR, wherein a representative sample having been deposited under Accession Number NCIMB 42171.

* * * * *